(12) United States Patent
Lanza et al.

(10) Patent No.: US 7,220,401 B2
(45) Date of Patent: *May 22, 2007

(54) BLOOD CLOT-TARGETED NANOPARTICLES

(75) Inventors: Gregory Lanza, St. Louis, MO (US); Samuel A. Wickline, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/225,024

(22) Filed: Aug. 20, 2002

(65) Prior Publication Data

US 2003/0086867 A1 May 8, 2003

Related U.S. Application Data

(63) Continuation-in-part of application No. 09/404,963, filed on Sep. 24, 1999, now Pat. No. 6,548,046.

(51) Int. Cl.
*A61B 5/055* (2006.01)
(52) U.S. Cl. .................. 424/9.323; 424/9.32
(58) Field of Classification Search ......... 424/9.52, 424/9.51, 9.5, 1.21, 1.29, 9.32, 9.323, 450, 424/455, 489; 514/937
See application file for complete search history.

(56) References Cited

U.S. PATENT DOCUMENTS

| | | | |
|---|---|---|---|
| 5,077,036 A | 12/1991 | Long, Jr. ................. 424/5 |
| 5,114,703 A | 5/1992 | Wolf et al. ............... 424/5 |
| 5,271,928 A * | 12/1993 | Schneider et al. ......... 424/9.51 |
| 5,401,634 A | 3/1995 | Milbrath ................ 435/6 |
| 5,512,294 A | 4/1996 | Li et al. ................ 424/450 |
| 5,536,489 A | 7/1996 | Lohrmann et al. ......... 424/9.52 |
| 5,542,935 A | 8/1996 | Unger et al. ............. 604/190 |
| 5,690,907 A | 11/1997 | Lanza et al. ............. 424/9.5 |
| 5,780,010 A | 7/1998 | Lanza et al. ............. 424/9.32 |
| 5,958,371 A | 9/1999 | Lanza et al. ............. 424/1.21 |
| 6,123,923 A * | 9/2000 | Unger et al. ............. 424/9.52 |
| 6,139,819 A * | 10/2000 | Unger et al. ............. 424/9.52 |
| 6,461,586 B1 * | 10/2002 | Unger ................. 424/9.32 |
| 6,821,506 B2 * | 11/2004 | Lanza et al. ............. 424/9.3 |

FOREIGN PATENT DOCUMENTS

| | | |
|---|---|---|
| DE | 4232755 | 3/1994 |
| EP | 0251494 | 1/1988 |
| EP | 0727225 | 8/1996 |
| EP | 0274431 | 7/1998 |
| WO | WO 95/03829 | 2/1995 |
| WO | WO 96/40285 | 12/1996 |

OTHER PUBLICATIONS

Flacke et al. "Novel MRI Contrast Agent for Molecular Imaging of Fibrin: Implications for Detecting Vulnerable Plaques" Circulation 104:1280-1285 (2001).
Hnatowich et al. "Investigation of Avidin and Biotin for Imaging Applications" Journal of Nuclear Medicine 28(8):1294-1302 (1987).
Hudson et al. "Red Cell Volume and Cardiac Output in Anemic Preterm Infants" Archives of Disease in Childhood 65(7):672-675 (1990).
Lanza et al. "Specific Acoustic Enhancement of Vascular Thrombi In Vivo with a Novel Site Targeted Ultrasonic Contrast Agent" Circulation 92(8 Suppl.):1260 (1995).
Lanza et al. "Initial Description and Validation of a Novel Site Targeted Ultrasonic Contrast Agent" Circulation 92 (8 Suppl.):1260 (1995).
Lanza et al. "A Novel Site-Targeted Ultrasonic Contrast Agent with Broad Biomedical Application" Circulation 94(12):3334-3340 (1996).
Lanza et al. "High-Frequency Ultrasonic Detection of Thrombi with a Targeted Contrast System" Ultrasound in Medicine and Biology 23(6):863-870 (1997).
Muzykantov et al. "Immunotargeting of Streptavidin to the Pulmonary Enjdothelium" Journal of Nuclear Medicine 35(8) (1994).
Wallace et al. "Intravascular Ultrasound Detection of Thrombi After Enhancement with a Novel Site Targeted Acoustic Contrast Agent" Circulation 92(8 Suppl.):1585 (1995).

* cited by examiner

*Primary Examiner*—Dameron L. Jones
(74) *Attorney, Agent, or Firm*—Morrison & Foerster LLP

(57) ABSTRACT

Emulsions comprising nanoparticles formed from high boiling perfluorochemical substances, said particles coated with a lipid/surfactant coating are made target-specific by directly coupling said nanoparticles to a targeting ligand. The nanoparticles may further include biologically active agents, radionuclides, and/or other imaging agents.

13 Claims, 1 Drawing Sheet

BLOOD CLOT-TARGETED NANOPARTICLES

CROSS-REFERENCE TO RELATED APPLICATIONS

This is a continuation-in-part of U.S. Ser. No. 09/404,963 filed Sep. 24, 1999 now U.S. Pat. 6,548,046 and now pending. The contents of this application are incorporated herein by reference.

FIELD OF THE INVENTION

The invention is directed to nanoparticles which home to specific blood clots and which carry to these targets substances useful in diagnosis or treatment. More specifically, the invention concerns nanoparticles to which ligands specific for thromboses are directly bound and which further contain imaging agents and/or bioactive materials.

BACKGROUND ART

U.S. Pat. Nos. 5,690,907, 5,780,010 and 5,958,371, the disclosures of which are incorporated herein by reference, describe biotinylated lipid-encapsulated perfluorocarbon nanoparticles which are useful for the delivery of radionuclides, and magnetic resonance imaging agents to specific locations through a biotin-avidin system. Bioactive agents may also be included. In this approach, the target location is coupled to a target-specific ligand which is also coupled to biotin. Avidin is then employed to bridge the now biotinylated target with biotin derivatized nanoparticles contained in an emulsion. Included among the targets are blood clots; however, these blood clots are first labeled with antifibrin antibodies to which biotin is then bound. No direct targeting of blood clots with ligands specific for such clots is disclosed.

This is in contrast to the compositions of the present invention wherein a ligand specific for thromboses is directly coupled, initially, to the nanoparticles in the emulsion. Thus, the emulsion, when administered, is target-specific by virtue of bearing the target-specific ligand at its surface.

Fluorochemical emulsions with specification binding moieties have been described in U.S. Pat. No. 5,401,634 for use as labels in in vitro analytical procedures. However, in vivo uses, for example, for acoustic imaging, drug delivery or delivery of imaging agents or nuclides is not contemplated. In addition, consistent with the failure to envision in vivo use, no modification of these particles for binding to thromboses is mentioned.

Others have described drug delivery using particulate supports which differ from the nanoparticles of the present invention. For example, PCT publication WO95/03829 describes oil emulsions where the drug is dispersed or solubilized inside an oil droplet and the oil droplet is targeted to a specific location by means of a ligand. U.S. Pat. No. 5,542,935 describes site-specific drug delivery using gas-filled perfluorocarbon microspheres. The drug delivery is accomplished by permitting the microspheres to home to the target and then effecting their rupture. Low boiling perfluoro compounds are used to form the particles so that the gas bubbles can form.

In contrast to the compositions described above, the compositions of the invention are ligand-bearing liquid emulsions based on high boiling perfluorocarbon liquids. The compositions of the invention provide facile means to deliver materials contained in their surface to blood clots.

An article reporting the work of the present inventors, Flacke, S., et al., *Circulation* (2001) 104:1280–1285 appeared in September of 2001 and described molecular imaging of thrombus using nanoparticles formulated with GD-DTPA-BOA. The particles were covalently coupled to antifibrin monoclonal antibody and used to obtain magnetic resonance images of blood clots.

The present invention expands the concept set forth in this article and provides nanoparticles which target blood clots specifically and which may provide, in addition to magnetic resonance imaging agents, means for acoustic imaging, therapeutic agents, and radionuclides.

DISCLOSURE OF THE INVENTION

The invention provides compositions which are liquid emulsions. The liquid emulsions contain nanoparticles comprised of liquid, relatively high boiling perfluorocarbons surrounded by a coating which is composed of a lipid and/or surfactant. The surrounding coating is able to couple directly to a moiety that targets blood clots or can entrap an intermediate component which is covalently coupled to the said moiety, optionally through a linker. Alternatively, the coating may be cationic so that negatively charged blood clot targeting agents such as nucleic acids, in general or aptamers, in particular, can be adsorbed to the surface.

In addition to the targeting agent or ligand, the nanoparticles may contain at their surface a radionuclide, a contrast agent for magnetic resonance imaging (MRI) and/or a biologically active compound. The nanoparticles themselves can serve as contrast agents for ultrasound imaging.

As the emulsions of the invention are intended to target blood clots or thromboses, especially in vivo, components of these clots are used as suitable targets. Among these markers or targets are fibrin, tissue factor, gpIIb/IIIa, tissue factor/VIIA complex, activated clotting factor Xa, activated clotting factor IXa, and the fibrin condensation product, d-dimer. Tissue factor is present but not preferred as it is relatively nonspecific.

Thus, in one aspect, the invention is directed to a composition comprising an emulsion of liquid, high boiling perfluorocarbon-based nanoparticles, said nanoparticles further comprising a coating of a lipid/surfactant in which is embedded, or to which is directly covalently bound at least one ligand that targets blood clots, and optionally at least one biologically active compound, at least one radionuclide, and/or at least one imaging agent.

In other aspects, the invention is directed to methods to administer drugs to, and to obtain images of blood clots, especially in vivo, using the compositions of the invention.

MODES OF CARRYING OUT THE INVENTION

Figure 1:
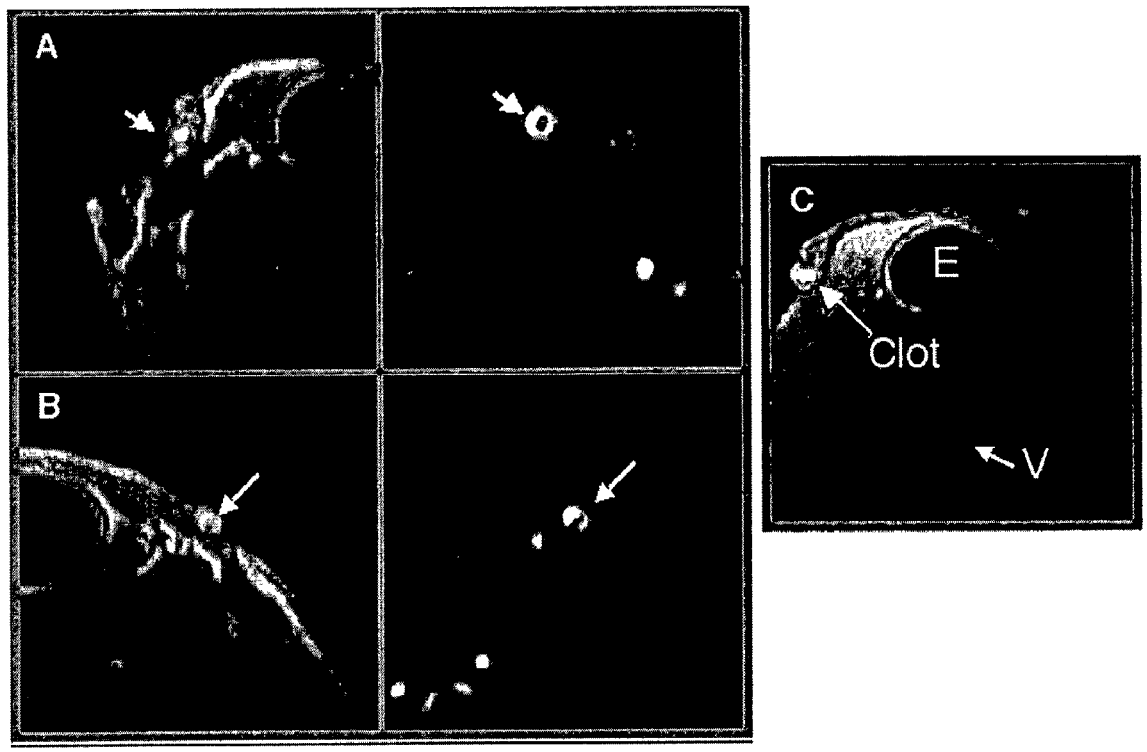
FIGS. 1A and 1B show acoustic images obtained with fibrin-specific and non-fibrin-specific paramagnetic nanoparticles respectively.
FIG. 1C shows similar images but with fat suppression.

The carrier system that is the basis for the present invention is a nanoparticulate system containing a high boiling perfluorocarbon as a core and an outer coating that is a lipid/surfactant mixture which provides a vehicle for binding a multiplicity of copies of one or more desired components to the nanoparticle. The construction of the basic particles and the formation of emulsions containing them, regardless of the components bound to the outer surface is described in the above-cited patents to the present applicants, U.S. Pat. Nos. 5,690,907; 5,780,010; and patents issued on daughter applications U.S. Pat. Nos. 5,989,520 and 5,958,371 and incorporated herein by reference.

The high boiling fluorochemical liquid is such that the boiling point is higher than that of body temperature—i.e., 37° C. Thus, fluorochemical liquids which have boiling points at least 30° C. are preferred, more preferably 37° C., more preferably above 50° C., and most preferably above about 90° C. The "fluorochemical liquids" useful in the invention include straight and branched chain and cyclic perfluorocarbons including perfluorinated compounds which have other functional groups. Perfluorinated compounds are preferred. Particularly preferred are compounds which will remain in the liquid state when they serve their function in the subject; for example, when used to obtain an acoustic image.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether.

The coating which comprises lipid/surfactant to form an outer coating on the nanoparticles which will contain the coupled ligand or entrap reagents for binding desired components to the surface include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids included in the outer layer may be advantageous in entrapping ligands such as nucleic acids, in particular aptamers. Typical cationic lipids may include DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol,1,2-diacyl-3-trimethylammonium-propane; 1,2-diacyl-3-dimethylammonium-propane; 1,2-diacyl-sn-glycerol-3-ethyl phosphocholine; and 3β-[N',N'-dimethylaminoethane)-carbamol]cholesterol-HCl.

The lipid/surfactant coated nanoparticles are typically formed by microfluidizing a mixture of the fluorocarbon lipid which forms the core and the lipid/surfactant mixture which forms the outer layer in suspension in aqueous medium to form an emulsion. Sonication or other techniques may be required to obtain a suspension of the lipid/surfactant in the aqueous medium. Typically, at least one of the components of the lipid/surfactant outer layer comprises a linker or functional group which is useful to bind the targeting ligand or the targeting ligand may already be coupled to the component at the time the emulsion is prepared. The components of the outer layer may also be coupled to imaging agents or radionuclides. The components may also include biologically active materials.

For coupling by covalently binding the targeting ligand or other organic moiety (such as a chelating agent for a paramagnetic metal) to the components of the outer layer, various types of bonds and linking agents may be employed. Typical methods for forming such coupling include formation of amides with the use of carbodiamides, or formation of sulfide linkages through the use of unsaturated components such as maleimide. Other coupling agents include, for example, glutaraldehyde, propanedial or butanedial, 2-iminothio lane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl) cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. A multiplicity of ways to couple, covalently, a desired ligand to one or more components of the outer layer is well known in the art. The ligand itself may be included in the surfactant layer if its properties are suitable. For example, if the ligand contains a highly lipophilic portion, it may itself be embedded in the lipid/surfactant coating. Further, if the ligand is capable of direct adsorption to the coating, this too will effect its coupling. For example, nucleic acids, because of their negative charge, adsorb directly to cationic surfactants.

By "direct binding" of the ligand to the nanoparticle is meant that the ligand specific for a component characteristic of blood clots is associated with the nanoparticle itself, as opposed to indirect binding effected through biotin/avidin. In the biotin/avidin mediated targeting methods of the art, the clot-specific ligand is coupled not to the emulsion, but rather coupled, in biotinylated form to the targeted tissue. A component "characteristic of" blood clots does not include tissue factor.

The targeting ligands cover a range of suitable moieties which bind to components of blood clots. In general, a component may itself be used to generate a ligand by using the component to raise antibodies or to select aptamers that are specific binding partners for the component. Alternatively, a suitable ligand may be known in the art. More generically, however, antibodies can be raised to desired components by conventional techniques and can be provided, preferably, as monoclonal antibodies or fragments thereof, or as single chain antibodies produced recombinantly. If the subject to be administered the compositions of the invention is human, it may be desirable to humanize antibody-type ligands using techniques generally known in the art. Further, suitable proteins which bind to targets can be discovered through phage-display techniques or through the preparation of peptide libraries using other appropriate methods. Selective aptamers which are able selectively to bind desired targets may also be prepared using known techniques such as SELEX™. (Aptamers are oligonucleotides which are selected from random pools for their ability to bind selected targets.)

In addition to the foregoing, peptidomimetics, which are small organic molecules intended to mimic peptides of known affinities can also be used as targeting agents. Particularly preferred are targeting agents that bind to fibrin, as fibrin is a particularly characteristic element included in blood clots. Antifibrin antibodies are particularly preferred, including fragments thereof, such as the $F_{ab}$, $F_{(ab')2}$ fragments, single chain antibodies ($F_v$) and the like. In one preferred embodiment, when the emulsion includes an MRI imaging agent, such as a chelated transition metal, the targeting agent targets components of the blood clot other than fibrin, such as gpIIb/IIIa, clotting factors Xa and IXa and the like.

In addition to the ligand designed to bind the emulsion to blood clots, additional components of the emulsion can be bound to the nanoparticles in ways similar to those which are used to bind the ligands.

Other components which maybe coupled to the nanoparticles through entrapment in the coating layer include radionuclides. These radionuclides include, for example, $^{99}$Tc. The radioactive ions can be provided to the preformed emulsion in a variety of ways. For example, $^{99}$Tc-pertechnate may be mixed with an excess of stannous chloride and incorporated into the preformed emulsion of nanoparticles, followed by removal of unbound $^{99}$Tc-pertechnate by repeated centrifugation and washing. Stannous oxinate can be substituted for stannous chloride. In addition, commercially available kits, such as the HM-PAO (exametazine) kit marketed as Ceretek® by Nikomed Amersham can be used. Means to attach various radioligands to the nanoparticles of the invention are understood in the art.

In addition to incorporation of radionuclides, chelating agents containing paramagnetic metals for use in magnetic resonance imaging can also be employed. Typically, a chelating agent containing a paramagnetic metal is associated with the lipids/surfactants of the coating on the nanoparticles and incorporated into the initial mixture which is sonicated. The chelating agent can be coupled directly to one or more of components of the coating layer. Suitable chelating agents include a variety of multi-dentate compounds including EDTA, DPTA, and the like. These chelating agents can be coupled directly to functional groups contained in, for example, phosphatidyl ethanolamine, bis-oleate, and the like.

The paramagnetic metals useful in the MRI contrast agents of the invention include rare earth metals, typically, lanthanum, ytterbium, gadolinium, europium, and the like. Iron ions may also be used.

Also included in the surface of the nanoparticle, in some embodiments of the invention, are biologically active agents. These biologically active agents can be of a wide variety, including proteins, nucleic acids, pharmaceuticals, and the like. Thus, included among suitable pharmaceuticals are antineoplastic agents, hormones, analgesics, anesthetics, neuromuscular blockers, antimicrobials or antiparasitic agents, antiviral agents, interferons, antidiabetics, antihistamines, antitussives, anticoagulants, and the like.

In a typical procedure for preparing the emulsions of the invention, the fluorochemical liquid and the components of the lipid/surfactant coating are fluidized in aqueous medium to form an aqueous emulsion. The functional components of the surface layer may be included in the original emulsion, or may later be covalently coupled to the surface layer subsequent to the formation of the nanoparticle emulsion. In one particular instance, for example, where a nucleic acid targeting agent or drug is to be included, the coating may employ a cationic surfactant and the nucleic acid adsorbed to the surface after the particle is formed.

When appropriately prepared, the particles contain a multiplicity of functional reagents at their outer surface, the nanoparticles typically contain thousands of molecules of the biologically active agent, targeting ligand, radionuclide and/or MRI contrast agent. Desirably, the number of copies of a component to be coupled to the nanoparticle is in excess of 1,000 copies per particle, more preferably 5,000 copies per particle, still more preferably 10,000, and still more preferably 50,000 copies per particle.

In general, the targeted particles, directly coupled to a target-specific ligand, are useful themselves as ultrasound contrast agents. However, the inclusion of other components in multiple copies renders them useful in other respects. For instance, the inclusion of a chelating agent containing a paramagnetic ion makes the emulsion useful as a magnetic resonance imaging contrast agent. Because the particles comprise large amounts of fluorine, the addition of a paramagnetic ion is not necessary to make these particles useful for MRI. The inclusion of biologically active materials makes them useful as drug delivery systems. The inclusion of radionuclides makes them useful either as therapeutics for radiation treatment or as diagnostics for imaging or both. A multiplicity of such activities may be included; thus, images can be obtained of targeted tissues at the same time active substances are delivered to them. Finally, because the particles have a fluorocarbon core, $^{19}$F magnetic resonance imaging can be used to track the location of the particles concomitantly with their additional functions described above.

The emulsions can be prepared in a range of methods depending on the nature of the components to be included in the coating. In a typical procedure, used for illustrative purposes only, the following procedure is set forth: Perfluorooctylbromide (40% w/v, PFOB, 3M), and a surfactant co-mixture (2.0%, w/v) and glycerin (1.7%, w/v) is prepared where the surfactant co-mixture includes 64 mole % lecithin (Pharmacia Inc), 35 mole % cholesterol (Sigma Chemical Co.) and 1 mole % dipalmitoyl-L-alpha-phosphatidyl-ethanolamine, Pierce Inc.) dissolved in chloroform. A drug is suspended in methanol (~25 μg/20 μl) and added in titrated amounts between 0.01 and 5.0 mole % of the 2% surfactant layer, preferably between 0.2 and 2.0 mole %. The chloroform-lipid mixture is evaporated under reduced pressure, dried in a 50° C. vacuum oven overnight and dispersed into water by sonication. The suspension is transferred into a blender cup (Dynamics Corporation of America) with perfluorooctylbromide in distilled or deionized water and emulsified for 30 to 60 seconds. The emulsified mixture is transferred to a Microfluidics emulsifier (Microfluidics Co.) and continuously processed at 20,000 PSI for three minutes. The completed emulsion is vialed, blanketed with nitrogen and sealed with stopper crimp seal until use. A control emulsion can be prepared identically excluding the drug from the surfactant commixture. Particle sizes are determined in triplicate at 37° C. with a laser light scattering submicron particle size analyzer (Malvern Zetasizer 4, Malvern Instruments Ltd., Southborough, Mass.), which indicate tight and highly reproducible size distribution with average diameters less than 400 nm. Unincorporated drug can be removed by dialysis or ultrafiltration techniques. To provide the targeting ligand, an $F_{(ab)}$ fragment is coupled covalently to the phosphatidyl ethanolamine through a bifunctional linker in the procedure described above.

The following examples are intended to illustrate but not to limit the invention.

EXAMPLE 1

Preparation of Nanoparticles

Nanoparticles are prepared that comprise perfluorooctylbromide (40% w/v, PFOB), a surfactant co-mixture (2.0%, w/v) and glycerin (1.7%, w/v) and optionally an "oil" (2 to 10% w/v, substituted for the PFOB).

For various applications, the surfactant co-mixture includes therapeutic agents, dipalmitoylphosphatidyl choline, cholesterol, phosphoethanolamine-N-4 PEG(2000)-(p-maleimidophenyl)butyramide (MPB-PEG-PE) or phosphoethanolamine-(pmaleimidophenyl)butyramide, phosphatidylethanolamine, and sphingomyelin in varying molar ratios, which are dissolved in chloroform/methanol, evaporated under reduced pressure, dried in a 50° C. vacuum oven overnight and dispersed into water. For paramagnetic formulations, the surfactant co-mixture includes varying amounts of gadolinium lipophilic chelates such as gadolinium diethylene-triamine-pentaacetic acid-bis-oleate (Gd-DTPA-BOA) or gadolinium diethylene-triamine-pentaacetic acid-phosphatidylethanolamine (Gd-DTPA-PE) at overall concentrations of 0, to 50 mole %.

Oil (i.e., vegetable oil, vitamin E or other biocompatible "oil") may be added alone or may incorporate therapeutic agents. Lipophilic and hydrophobic therapeutic agents may be dissolved into the oil component up to supersaturating concentrations to increase total drug payload.

The above suspension is combined with PFOB and distilled, deionized water, blended and then emulsified at 10,000–20,000 PSI for three minutes.

The thiolated ligands are coupled to the maleimide derivatized phospholipid (or lipophilic substitute) in 50 mM phosphate, 10 mM EDTA buffer at pH 6.65 overnight under an nonoxidative atmosphere (i.e., nitrogen, argon). Small peptides and nonpeptide molecules are coupled to the lipid moiety prior to emulsification.

Antibodies are reacted with N-succinimidyl S-acetylthioacetate (SATA) for 30 min, dialyzed overnight, deprotected with hydroxylamine, dialyzed in oxygen free buffers, then coupled to the nanoparticles at room temperature. Alternatively, antibodies are enzymatically digested with papain or pepsin to yield $F_{(ab)}$ fragments isolated by routine affinity chromatography.

Particle sizes are determined in triplicate at ambient temperature with a laser light scattering submicron particle size analyzer (Malvern Zetasizer 4, Malvern Instruments Ltd, Southborough, Mass.), which typically indicates a highly reproducible size distribution with average diameters around 250 nm.

EXAMPLE 2

Targeting Canine in Situ Fibrin in Vivo

A perfluorocarbon nanoparticle contrast agent incorporates 1,2-dipalmitoyl-sn glycero-3-phosphoethanolamine-N-4-(p-maleimidophenyl)butyramide (MPB-PE; Avanti Polar Lipids, Alabaster, Ala.) into the outer lipid monolayer of the emulsion to accommodate subsequent ligand conjugation. Gd-DTPA-phosphatidylethanolamine (Gd-DTPA-PE) was added to the surfactant mixture at 0 or 20 mole % as described above.

Anti-fibrin monoclonal antibody (NIB 1H10, NIB SF3) is produced and purified by conventional methods. A fibrin-targeted nanoparticle contrast agent is created by the covalent bonding of anti-fibrin $F_{(ab)}$' fragments to the outer lipid membrane surface. Anti-fibrin $F_{(ab)}$' fragments are generated (Pierce, Rockford, Ill.) and combined with the MPB-PE derivatized emulsion (1–2 mg $F_{(ab)}$'/ml of 40% perfluorocarbon emulsion) at pH 6.7 under nitrogen overnight. The conjugated nanoparticles are dialyzed, vialed and stored at 4° C. A nonspecific control emulsion is prepared using irrelevant IgG $F_{(ab)}$' fragments.

The detection of clots in a flowing intravascular environment is evaluated in canines. Thrombi are formed within the open circulation, targeted with system in situ within isolated vascular segments, then exposed to the systemic circulation for magnetic resonance imaging. Animal protocols are approved by the Animal Studies Committee at Washington University.

Two dogs (~20 kg) were pretreated with tranexamic acid (0.25 g/hr) to inhibit endogenous thrombolysis. Each animal was anesthetized (sodium pentathol/isofluorane), prepped for surgery and the external jugular veins exposed. Nylon monofilament (4-0) with 10, 0.5 cm strands of thrombin-soaked cotton fibers were positioned by ultrasound (Acuson Sequoia, Mountainview, Calif.). Following clot formation, thrombi were entrapped between snare closures and one ml of fibrin-targeted gadolinium or control nanoparticles was infused into the isolated segment. After contrast incubation (1 hr), the thrombi were reintroduced to the general circulation and imaged. At the conclusion of the acute procedure, animals were euthanized and the vessels retrieved for routine immunohistopathology of fibrin within the thrombus.

Canine thrombi created within the external jugular vein were imaged-with a 3-D, fat-suppressed, T1-weighted fast gradient echo (TE/TR/a: 8.1/24/35f, FOV 180 mm, matrix 205×256). Flow within vessels and thrombi (as a flow deficit) were imaged with a 3-D phase contrast, T1-weighted fast gradient echo angiogram (TE/TR/a: 5.3/15/15f, FOV 200 mm, matrix 192×256).

The magnitude of contrast-enhancement expected in vivo with open circulation conditions was evaluated in dogs. Control or 20 mole % (Gd-DTPA-PE) anti-fibrin nanoparticles were administered to thrombus created within the external jugular vein. Thrombus was imaged with a 3-D T1-weighted, fat suppression, fast gradient echo sequence and detectability of targeted clot was markedly enhanced by the fibrin-specific paramagnetic nanoparticles relative to control thrombus (FIGS. 1A and 1B). Phase contrast angiography revealed the clots as flow deficits in both external jugular veins. Corresponding gradient echo images revealed a selective enhancement of the treated clot yielding a signal intensity (1780±327) higher than the bright fat signal (1360±140), whereas, the control clot had a signal intensity (815±41) similar to that of the adjacent muscle (768±47). On TI-weighted gradient recalled echo images with fat suppression, the targeted clot showed the brightest image signal (FIG. 1C). The CNR between the targeted clot and blood using nanoparticles with 20 mole % Gd-DTPA measured with this sequence was approximately 118±21. The CNR between the targeted clot and the control clot was 131±37. Fibrin immunostaining of the excised vessel and clot confirmed the abundance and localization of fibrin corresponding to the contrast enhancement in vivo.

EXAMPLE 3

Targeting Canine Circulating Fibrin

The perfluorocarbon nanoparticle contrast agent used in vivo (circulating) was produced by incorporating 1,2-dipalmitoyl-sn glycero-3-phosphoethanolamine-N-4-(p-maleimidophenyl)butyramide (MPB-PE; Avanti Polar Lipids, Alabaster, Ala.) into the outer lipid monolayer of the emulsion to accommodate subsequent ligand conjugation 20. Gd-DTPA-phosphatidylethanolamine (Gd-DTPA-PE) was added to the surfactant mixture at 20 mole % as described above.

Anti-fibrin monoclonal antibody (NIB 1H10, NIB 5F3) was produced and purified. A fibrin-targeted nanoparticle contrast agent was created by the covalent bonding of anti-fibrin $F_{(ab)}$' fragments to the outer lipid membrane surface. Anti-fibrin $F_{(ab)}$' fragments were generated (Pierce, Rockford, Ill.) and combined with the MPB-PEG-PE derivatized emulsion (1–2 mg $F_{(ab)}$'/ml of 40% perfluorocarbon emulsion) at pH 6.7 under nitrogen overnight. The conjugated nanoparticles were dialyzed, vialed and stored at 4° C.

Two dogs (20 kg) were pretreated with tranexamic acid (0.25 g/hr) to inhibit endogenous thrombolysis. Each animal was anesthetized (sodium pentathol/isofluorane), prepped for surgery and the external jugular veins exposed. Nylon monofilament (4-0) with 10, 0.5 cm strands of thrombin-soaked cotton fibers were positioned by ultrasound (Acuson Sequoia, Mountainview, Calif.). Following clot formation, thrombi were entrapped between snare closures and one ml of fibrin-targeted gadolinium or control nanoparticles was infused into the isolated segment. After contrast incubation (1 hr), the thrombi were reintroduced to the general circulation and imaged. At the conclusion of the acute procedure, animals were euthanized and the vessels retrieved for routine immunohistopathology of fibrin within the thrombus. Canine thrombi within the external jugular vein were imaged with a 3-D, fat-suppressed, Ti-weighted fast gradient echo (TE/TR/a: 8.1/24/35f, FOV 180 mm, matrix 205×256). Fibrin-targeted paramagnetic nanoparticles were injected intravenously through peripheral access. After 30 minutes, T1-weighted contrast of the clot was noted. Contrast single level continued to increase up to 60 minutes.

EXAMPLE 4

Coupling Antibody to Fibrin to Perfluorocarbon Emulsion Particle

Preparation of Emulsion: The perfluorocarbon nanoparticle contrast agent is, produced by incorporating 1,2-dipalmitoyl-sn-glycero-3-phosphoethanolamine-N-4-(p-maleimidophenyl)butyramide (MPB-PE) into the outer lipid monolayer of the emulsion. The emulsion is comprised of perfluorodichlorooctane, safflower oil, a surfactant co-mixture and glycerin. The surfactant co-mixture includes lecithin, cholesterol and MPB-PE which is dissolved in chloroform. The chloroform-lipid mixture is evaporated under reduced pressure, dried in a 50° C. vacuum oven overnight and dispersed into water by sonication. The suspension is transferred into a blender cup with perfluorodichlorooctane, safflower oil and distilled, deionized water and emulsified for 30 to 60 seconds. The pre-emulsified mixture is transferred to a microemulsifier and continuously processed at 10,000 PSI for three minutes. The completed emulsion is vialed, blanketed with nitrogen and sealed with stopper crimp seal until use. A negative control emulsion is prepared identically, except a nonderivatized phosphatidylethanolamine is substituted into the surfactant co-mixture. Particle sizes are determined in triplicate at 30° C. with a laser light scatter submicron particle size analyzer.

Conjugation of fibrin $F_{(ab)}$' With MPB-PE Derivatized Emulsion: $F_{(ab)}$' fractions are pooled and combined with the MPB-PE derivatized emulsion (0.01 to 5.0 mg $F_{(ab)}$'/ml of emulsion, preferably 1 to 2 mg $F_{(ab)}$'/ml of emulsion). The mixture is adjusted to pH 6.7, sealed under nitrogen and allowed to react overnight at ambient temperatures with gentle, continuous mixing. The mixture may be subsequently dialyzed with a 300,000 MWCO Spectra/Por DispoDialyzer (Laguna Hills, Calif.) against 10 mM phosphate buffer (pH 7.2) to remove unconjugated $F_{(ab)}$' fragments. The final emulsion is vialed under nitrogen and stored at 4° C. until use.

EXAMPLE 5

In Vitro Targeting of Fibrin-Rich Plasma Thrombi Using a Fibrin-Targeted, Acoustic Contrast System.

Whole blood was obtained fresh and anticoagulated (9:1, v/v) with sterile sodium citrate. In a series of trials, plasma clots (9) were produced by combining plasma and 100 mM calcium chloride (3:1, v/v) with 5 units of thrombin (Sigma Chemical Company, St. Louis, Mo.) in a plastic tube overlying nitrocellulose membranes. The plasma was allowed to coagulate slowly at room temperature.

Plasma clots were incubated with anti-fibrin ($F_{ab}$) conjugated or non-conjugated control emulsion contrast using antifibrin monoclonal antibodies (NIB-5F3 or NIB-1H10) (Tymkewycz, et al. (1992); Tymkewycz, et al. (1993)). Half of the clots (5) were incubated individually with 150 μg biotinylated antifibrin monoclonal antibody in 10 ml PBS with 1% bovine serum albumin, (crystallized, Sigma Chemical Company, St. Louis, Mo.) for two hours; the remaining clots (4) were maintained in PBS with 1% bovine serum albumin. Bovine serum albumin was added during antibody incubations to minimize nonspecific protein binding to the polystyrene petri dish walls. The anti-fibrin targeted emulsion was incubated with clots (0.2 ml) for 30 minutes. Control clots were treated similarly with a nontargeted control perfluorocarbon emulsion (0.2 ml) for 30 minutes. The plasma clots on nitrocellulose were insonified using an acoustic microscope to assess the change in ultrasonic backscattered power attributable to the control and targeted emulsions.

The microscope consisted of a 50 MHz broadband, focused, piezoelectric delay-line transduce (¼ inch diameter, ½ inch focal length, Model V390, Panametrics Co., Waltham, Mass.) operated in the pulse-echo mode. A Tektronix DSA 601 digitizing oscilloscope (Beaverton, Oreg.) was used to digitize backscattered radiofrequency data at 500 megasamples per second with 8-bit resolution. Radiofrequency data collected from each site was averaged 32 times. Averaged radiofrequency data were acquired from approximately 400 independent sites with 50 micron lateral step resolution. The radiofrequency data are stored in a low resolution raster scan format and analyzed with custom software. Segments of the radiofrequency lines, 500 nsec in duration and encompassing surface reflection are gated for analysis. The gated data are multiplied by a Hamming window and their power spectra determined by fast-Fourier transformation.

The power spectra from each specimen was referenced to the power spectrum backscattered from a near-perfect steel plate reflector to compute the apparent frequency-dependent backscatter transfer function. The backscatter transfer function for the acoustic reflectivity of the smooth cells, B(f), was expressed in decibels relative to the power reflected from the steel plate:

$$B(f)^2 = 10 \log[V_{(f)}^2{}_{tissue}/[V_{(f)}^2{}_{steel\ plate}]$$

where $V_{(f)}^2{}_{tissue}$ is the power at selected frequency of the gated rf backscattered from the cells and $V_{(f)}^2{}_{steel\ plate}$ is the power at the same frequency of the gated rf backscattered from the steel plate. Integrated backscatter (IB) was computed from the average of the frequency-dependent backscatter transfer function over the useful bandwidth of the transducer.

The invention claimed is:

1. A method to obtain a magnetic resonance image of a blood clot in a subject, which method comprises
    administering to said subject an emulsion of nanoparticles, said nanoparticles consisting of liquid perfluorocarbon coated with lipid/surfactant,
    wherein said nanoparticles are coupled to at least one targeting ligand that is specific for at least one component characterizing blood clots that binds specifically to fibrin, gpIIb/IIIa, tissue factor/VIIA complex, activated clotting factor Xa, activated clotting factor IXa, or the fibrin condensation product, d-dimer, and
    wherein said nanoparticles are also coupled to at least one magnetic resonance imaging (MRI) contrast agent;
    allowing the targeting ligand to bind to the blood clot; and
    detecting a magnetic resonance image of said blood clot wherein said blood clot is bound to said ligand coupled directly to said lipid/surfactant-coated particles, while said nanoparticles are entirely in the liquid state.

2. The method of claim 1, wherein said MRI contrast agent is a chelated paramagnetic ion.

3. The method of claim 2, wherein the paramagnetic ion is gadolinium ion.

4. The method of claim 1, wherein the perfluorocarbon is selected from the group consisting of perfluorodecalin, perfluorooctane, perfluorodichlorooctane, perfluoro-n-octyl bromide, perfluoroheptane, perfluorodecane, perfluorotripropylamine, perfluortributylamine, and mixtures thereof.

5. The method of claim 4, wherein the perfluorocarbon is perfluoro-n-octyl bromide.

6. The method of claim 1, wherein the targeting ligand is coupled covalently to a component of the lipid/surfactant coating.

7. The method of claim 1, wherein the ligand binds specifically to fibrin.

8. The method of claim 7, wherein said ligand is an antifibrin antibody or an immunoreactive fragment thereof.

9. The method of claim 1, wherein the ligand binds specifically to gpIIb/IIIa.

10. The method of claim 1, wherein the ligand binds specifically to tissue factor/VIIA complex.

11. The method of claim 1, wherein the ligand binds specifically to activated clotting factor Xa.

12. The method of claim 1, wherein the ligand binds specifically to activated clotting factor IXa.

13. The method of claim 1, wherein the ligand binds specifically to fibrin condensation product, d-dimer.

* * * * *